United States Patent [19]

Hirleman, Jr.

[11] 4,251,733
[45] Feb. 17, 1981

[54] TECHNIQUE FOR SIMULTANEOUS PARTICLE SIZE AND VELOCITY MEASUREMENT

[76] Inventor: Edwin D. Hirleman, Jr., 2008 E. Watson, Tempe, Ariz. 85283

[21] Appl. No.: 920,550

[22] Filed: Jun. 29, 1978

[51] Int. Cl.³ .......................................... G01N 15/06
[52] U.S. Cl. .................................. 250/575; 356/335
[58] Field of Search .......... 250/573, 574, 575, 223 R, 250/222 PC; 356/335, 336

[56] References Cited

U.S. PATENT DOCUMENTS

| | | | |
|---|---|---|---|
| 4,071,298 | 1/1978 | Falconer | 356/336 |
| 4,095,775 | 6/1978 | Hotham | 250/574 |
| 4,110,043 | 8/1978 | Eisert | 250/222 PC |

*Primary Examiner*—David C. Nelms

[57] ABSTRACT

Two beams of electromagnetic radiation with symmetric radial intensity distributions are directed through space. A particle sampling volume is defined by those portions of the two beams within the field of view of one or more radiation sensitive detectors. The detectors respond to scattered radiation or fluorescence from particles passing through the beams in the sampling volume. The detector output for a single particle indicates two signal pulses corresponding to those times when the particle was in one of the beams. The speed of the particle in the plane perpendicular to the beams is determined from the transit time or width of the signal pulses, and the angle of the particle traverse in that plane determined from the time-of-flight between the signal pulses. The speed and angle thereby determine two velocity components in the perpendicular plane. Then the exact particle trajectory is specified by the angle and one point on the trajectory which is determined from relative magnitudes of the signal pulses. This allows calculation of the radiation intensity incident on the particle throughout the trajectory from known radiation beam properties. A device then responds to the signal pulses to indicate the size or other physical properities of the particle without the ambiguity present if the incident radiation intensity is unknown.

14 Claims, 6 Drawing Figures

TECHNIQUE FOR SIMULTANEOUS PARTICLE SIZE AND VELOCITY MEASUREMENT

SUMMARY

The present invention is a technique for simultaneously measuring two velocity components and one or more physical properties (e.g. size and refractive index) of individual particles passing through two separated beams of radiation. In one possible embodiment the beams would be produced by a laser operating in the fundamental or $TEM_{00}$ mode such that the radial intensity distribution in the beams would be gaussian or normally distributed. In that case the magnitude of the particle velocity in the plane perpendicular to the two laser beams can be determined from the transit-time or time for the particle to pass through either beam of known diameter. This time is measured using detector(s) sensitive to scattered laser radiation or laser-induced fluorescence, two processes which are effectively instantaneous in relation to the transit-time.

Once the velocity magnitude is measured, the angle of the particle trajectory can be determined by measuring the time-of-flight or time for the particle to pass from one beam to the other. This time is also measured with detectors sensitive to radiation leaving the particle, either scattering or fluorescence. Specification of the velocity magnitude and angle are sufficient to allow two velocity components in the perpendicular plane to be determined with this invention. The optical system required is considerably simpler than prior methods for measuring two velocity components which might involve complex two-color or two-polarization laser Doppler velocimeters.

The remaining concepts of this invention permit simultaneous measurement of the size or other physical properties of the particle. Once the particle velocity components are determined the relative magnitudes of the signal pulses detected when the particle traversed each beam can be used to determine a point on the particle traverse and therefore the line of trajectory of the particle. Knowledge of the beam intensity distribution properties permits calculation of the radiation intensity level incident on the particle. With this invention particle properties can be unambiguously determined by normalizing absolute signal levels by the calculated incident intensity leaving only the particle properties effect on signal levels. The normalized signal levels are compared with a calibration standard to determine the particle properties of interest.

BACKGROUND AND PRIOR ART

The ability to measure simultaneously the size and velocity of individual particles or droplets in process flows is of considerable importance. Such measurements can be critical in evaluating particulate or smoke emissions, fuel spray combustion processes, and flow measurements in fluid systems. Prior to the invention of the laser both particle size and velocity measurements were made by physically placing a sample probe in the flow. The associated problems of flow interference and sampling errors can be eliminated using laser optical measurement techniques. The present invention concerns a laser method for simultaneous measurement of particle sizes and velocities.

The prior art in laser instruments for measuring particle velocity includes laser Doppler velocimeters, transit-time velocimeters and time-of-flight velocimeters. Laser Doppler velocimeters utilize two intersecting laser beams and are of no relevance here. The transit-time velocimeter (discussed by M. J. Rudd, in *Proceedings of Second International Workshop on Laser Velocimetry*, Purdue University Press, 1974, but apparently not patented) measures the time for a particle to pass across a single beam of known diameter thereby determining the particle velocity. The time-of-flight laser velocimeter (U.S. Pat. No. 3,941,477, R. Shodl, 1976) measures the time for a particle to pass between two beams of known spacing to determine the velocity. The transit-time method measures the magnitude of the velocity in the plane perpendicular to the laser beam but gives no information on the direction of particle motion. The time-of-flight method measures one particle velocity component along the interbeam axis in the plane normal to the two beams, but even this one component measurement is inaccurate if the beam spacing is not much greater than the beam diameters. The present invention includes a unique method to measure two velocity components in the perpendicular plane using a new analysis of the time-of-flight and transit-time velocimeters.

In terms of laser particle sizing instruments, a number have been invented which utilize the radiation scattered by particles passing through a laser beam for particle size measurements. Of relevance here is the nonuniform intensity distribution across a laser beam and the resulting ambiguity due to small particles passing through the center of the laser beam and large particles passing through off-center positions of lower beam intensity since both particles could scatter the same amount of laser radiation. This problem has been circumvented in the prior art by: physically confining the particles to pass only through the center of the laser beam (J. Heyder, *J. Aerosol Science*, 2,341, 1971); altering the laser beam intensity distribution (U.S. Pat. No. 3,851,169, F. R. Faxvog, 1974); or utilizing the ratio of light scattered by particles in two directions to cancel the incident intensity effect (U.S. Pat. No. 3,835,315, Grawatt, 1974). This invention includes a new and unique method to eliminate the ambiguity due to variations in incident intensity.

Another concept in particle measurements is to utilize laser-induced fluorescence rather than scattered radiation for both velocity (W. H. Stevenson, et. al., *Applied Physics Letters*, 27,395 (1975) and R. Shodl, "Laser Two Focus Velocimetry for Use in Aero Engines," AGARD Lecture Series 90, Trenton, N.J., August 25–27, 1977) and for particle sizing by the fringe visibility method (R. dos Santos and W. H. Stevenson, Applied Physics Letters, 30,236 (1977)). This concept can significantly enhance signal to noise ratios since stray laser scattering from windows or optical components which would provide a background noise level for scattering measurements can be optically filtered out. Scattering and fluorescence can be separated because in fluorescence molecules in the particle absorb some laser energy and jump to higher energy levels. After about $10^{-9}$ sec the excited molecules drop back down to a lower energy level and emit radiation (fluorescence), but the vast majority of molecules drop to energy levels above their initial state and therefore fluoresce at wavelengths longer than the laser or exciting wavelength. Therefore, a color filter which blocks the laser wavelength can pass fluorescent radiation. This invention includes the unique concept of utilizing fluorescent radiation levels for particle volume measurements.

Relative to the prior art, the present invention provides the unique and valuable capability to simultaneously measure particle velocities and sizes. The two velocity component measurement requires a considerably less complex system than methods presently available. Also, the present system is readily adapted for three dimensional velocity measurements.

DESCRIPTION OF THE INVENTION

Figure 1:
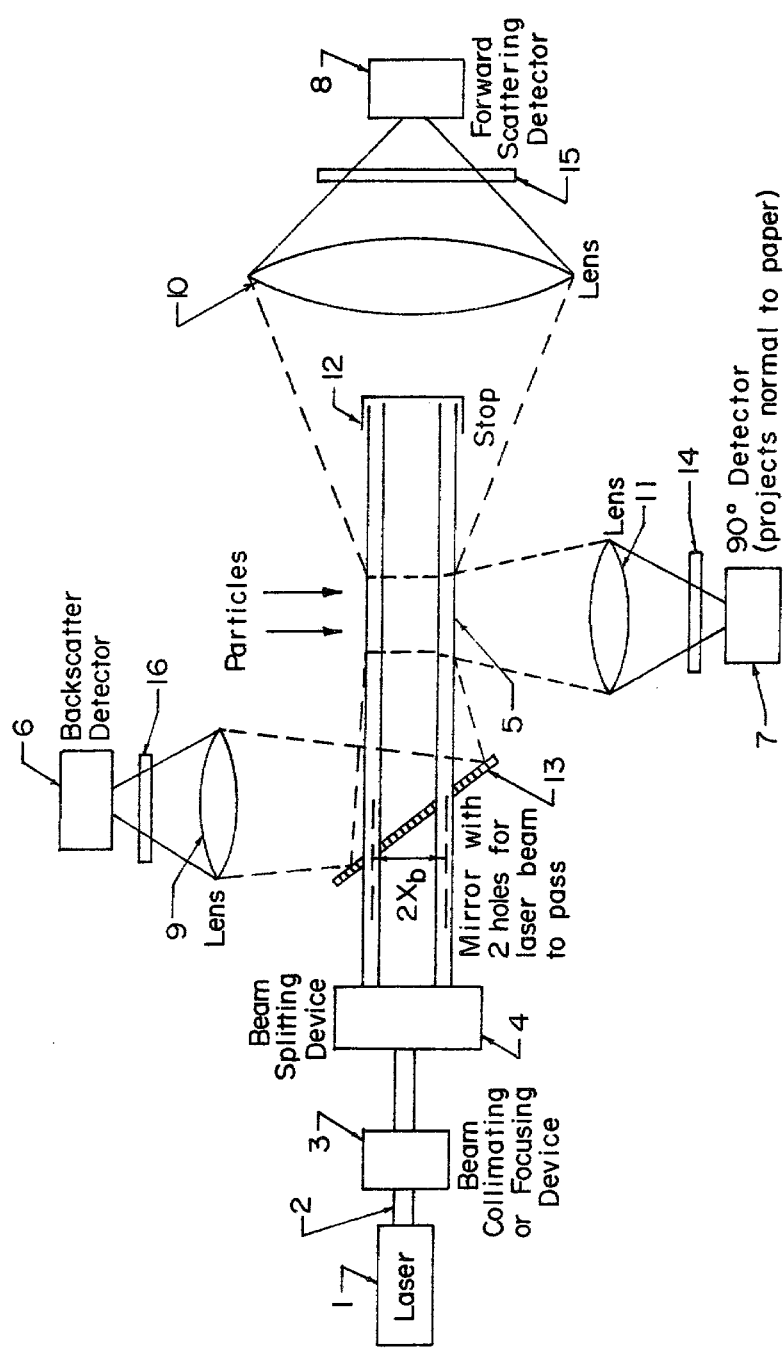
FIG. 1 shows several possible embodiments of the present invention.

FIG. 1 indicates an embodiment of the present invention. A laser 1 or other source generates a beam of electromagnetic radiation 2. The beam can be either collimated or focused by the device at 3. The laser should be operated in the fundamental mode (TEM$_{OO}$) such that there is a gaussian radial distribution of intensity across the laser beam. In that case the intensity distribution in any plane perpendicular to the beam propagation vector is given by:

$$\frac{I(r)}{I_o} = \exp(-2r^2/w^2) = \exp(-2(x^2 + y^2)/w^2) \quad (1)$$

where: $I(r)$ is the radiation intensity at a radial distance r from the beam or optical axis; x and y are cartesian coordinates; $I_o$ is the peak intensity at the beam center (r=0); w is the beam radius at the $1/e^2$ intensity points shown as circles 17, 30, in FIGS. 2 and 4; and these quantities can vary along the laser beam axis. The use of a non-laser source is possible if the radial intensity distribution is still exponential as described in Eq. (1). A beam splitting apparatus 4 (e.g. Kosters prism, ½ mirrors, etc.) then separates the original beam into two beams of approximately equal intensity. The intensities of the two beams need not be exactly equal but must be known. For convenience the present description assumes equal intensities but extension of the analysis to the general case is straightforward. Equal intensity beams can be obtained from a nonideal beamsplitter (not 50/50) by placing neutral density filters in the strongest beam until the intensities are equal.

Finally there is at least one detector (radiation to voltage converter) and associated optics which has within its field of view a region of space containing the two laser beams. If a focusing device is used at 3 the beams will focus or reach a minimum diameter at this sampling zone 5. Particles passing through the sampling zone scatter laser radiation and in some cases absorb the incident laser energy and spontaneously re-emit at longer wavelengths (fluorescence). The detector(s) 6, 7 and 8 collect this scattered or fluorescent radiation. It is also possible for the laser beams to be of different colors with a color sensitive detector viewing each beam. Optical filters 14, 15, 16 would be used to provide color selectivity. This configuration would indicate which beam a particle crossed first to determine the velocity direction.

Many possible detector configurations 6, 7 and 8 are applicable with the present invention. In general they are equally useful for the velocity component measurement since the radiation received and therefore detector outputs will all be proportional. The differentiation comes in terms of the particle property measurements where an absolute signal level magnitude rather than a relative or time-dependent quantity is of interest. A forward scattering configuration 8 is optimum for particle sizing when the refractive index is unknown, with collection angle defined by a stop 12 and the lens diameter 10. A backscatter arrangement 6 is advantageous if line of sight optical access is not available, for example, into a turbine where only one window would be available. Determination of particle properties such as shape or refractive index from laser scattering would utilize another configuration, for example a 90° detector 7. Since fluorescence is isotropic all detector configurations would work equally well for particle volume measurement with the present invention.

Figure 2:
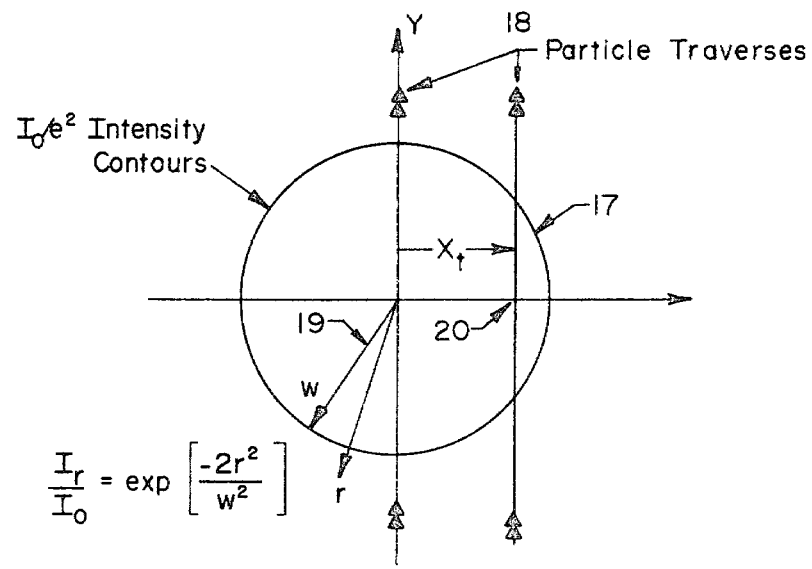
FIG. 2 indicates gaussian laser beam properties and two possible linear particle trajectories in the plane perpendicular to a laser beam.
Figure 3:
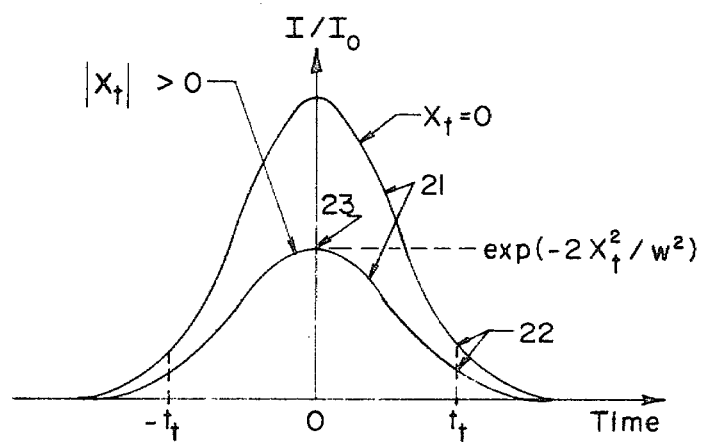
FIG. 3 indicates the time dependence of the laser intensity incident on the particle trajectories of FIG. 2. These curves are also proportional to the signals from the detectors of FIG. 1 for the particle trajectories of FIG. 2 assuming the scattering, fluorescence and detection processes to be effectively instantaneous.

FIG. 2 shows example constant velocity traverses across a single TEM$_{OO}$ laser beam. FIG. 3 indicates the corresponding incident intensity histories which are proportional gaussians with the same $1/e^2$ width. Since the light scattering, fluorescence, and detection processes are effectively instantaneous for most flow situations, FIG. 3 also indicates to within a constant factor the output history for any of the detectors 6, 7 and 8 for the traverses of FIG. 2. Now a particle traveling in a plane normal to the beam and parallel to the y-axis at some x traverse position $x_t$ 20 as in FIG. 2 will experience an incident intensity history:

$$I(x_t, y) = I_o \exp(-2x_t^2/w^2) \exp(-2y^2/w^2) \quad (2)$$

Note that any linear particle trajectory will fit Eq. (2) since the orientation of the x-y coordinate system is arbitrary. For a constant particle velocity in the perpendicular plane $V_\perp$ the position-time history referenced to y=0 will be y=$V_\perp$t. The temporal incident intensity and therefore scattered light (or fluorescence) detector response will then be:

$$I(x_t, t) = I_o \exp(-2x_t^2/w^2) \exp(-2V_\perp^2 t^2/w^2) \quad (3)$$

Since the first exponential is time-independent, scattered light signals from particles with linear, constant $V_\perp$ will always be proportional gaussians 21 with the same $1/e^2$ width as indicated in FIG. 3. Then the magnitude of the particle velocity $V_\perp$ in the plane perpendicular to a laser beam is uniquely determined by the transit-time $2t_t$ it takes for a particle to pass between the positions where the scattering signal is a given fraction 22 (e.g. $1/e^2$) of the peak signal value for that particle by:

$$V_\perp = \frac{w}{t_t} \tag{4}$$

regardless of the traverse position $x_t$. It is necessary to know a priori the beam diameter w 19 at the position where the particle traversed the laser beam. This can be accomplished either by utilizing a collimated beam (constant w) or by optically defining with the detector field-of-view a portion of a laser focus region which has approximately constant w. Both methods have proved successful in preliminary experiments performed with 70 μm glass microspheres falling at terminal velocity.

Figure 4:
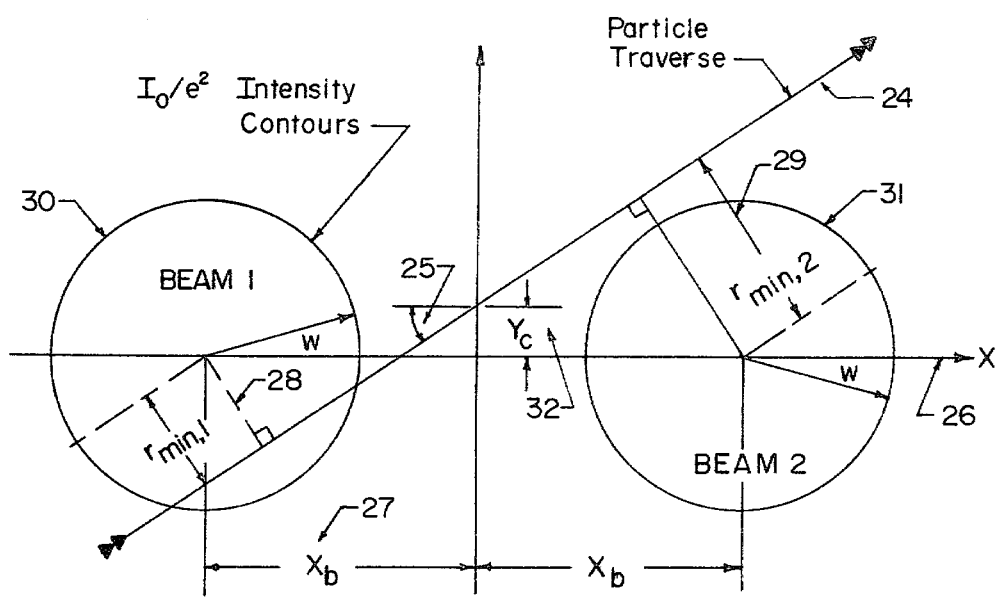
FIG. 4 presents a particle trajectory in the plane perpendicular to two gaussian laser beams.
Figure 5:
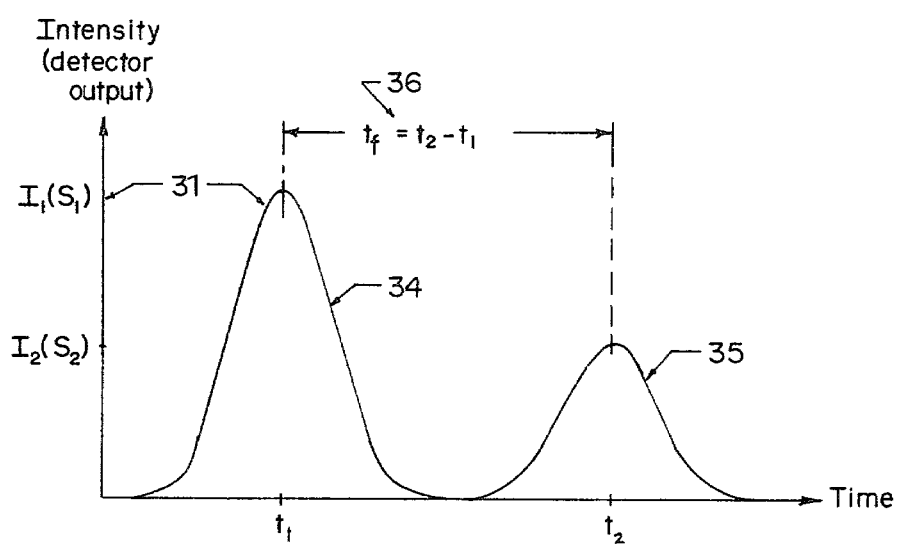
FIG. 5 indicates the time dependence of the laser intensity incident on the particle trajectory of FIG. 4. This curve is also proportional to the signal from the detectors of FIG. 1 assuming the scattering, fluorescence, and detection processes to be effectively instantaneous.

In order to separate the two velocity components in the perpendicular plane a second beam is utilized. FIG. 4 indicates the geometry of the system with an example particle traverse 24 in the normal plane but at some angle $\theta$ 25 relative to the plane of the laser beam axes 26. As a particle with constant, linear $V_\perp$ passes near the two beams, the incident intensity and therefore detector outputs will have peaks from both beams 34, 35 as shown in FIG. 5. Recall from the previous analysis that the gaussian signal from either beam can be used to determine the particle velocity magnitude in the perpendicular plane and therefore the time-of-flight $t_f$ 36 provides additional information. Prior art has used $t_f$ to determine a velocity but this prior art accepted errors due to nonzero traverse angle $\theta$ since:

$$t_f = 2x_b \cos\theta / V_\perp \tag{5}$$

from geometrical considerations. The measured time of flight $t_f$ then depends on the angle $\theta$ as well as the velocity and beam spacing $2x_b$. By independently measuring the velocity $V_\perp$ using Eq. (4) the absolute value of the traverse angle $\theta$ is uniquely determined from measured $t_f$ and Eq. (5). Two velocity components are then also fixed.

Considering Equation (5), note that $\cos\theta$ is a very weak function of $\theta$ for small $\theta$. Thus the uncertainty of determining $\theta$ from Equation (5) will be relatively high if the particle trajectory has $\theta$ near 0.0°, i.e. a trajectory nearly parallel to the x-axis in FIG. 4. In practice it is advantageous to orient the two beam centers at an angle of 20°–40° from the mean particle flow direction to optimize the accuracy of the measurement of the particle trajectory angle $\theta$. This would entail first determining the mean flow direction and then rotating the beams to the desired orientation.

The only remaining unknown quantity describing the particle traverse is the position $y_c$ 32 at which the reference or x axis 26 was crossed. This quantity is determined with the additional information of peak signal ratio $S_1/S_2$ also available from the detector output signature of FIG. 5 where:

$$\frac{S_1}{S_2} = \exp\left[\frac{8x_b y_c}{w^2} \sin\theta \cos\theta\right] \tag{6}$$

In Eq. (6) $y_c$ is the only remaining unknown after $V_\perp$ and then $\theta$ are found as discussed previously. Equation (6) assumes both beams are of constant $1/e^2$ diameter w in the region of the particle traverse but it can be easily re-derived for the case of different beam diameters $w_1$ and $w_2$. For simplicity, equal beam w's are assumed here.

Determination of $y_c$ is necessary to calculate the absolute peak intensity incident on a particle during a traverse. The maximum incident intensity from each beam occurs at the position of minimum perpendicular distance to the beam, $r_{min}$ 28, 29 in FIG. 4. This distance $$r_{min} = x_b \sin\theta \pm y_c \cos\theta \tag{7}$$

corresponding to beams 2 and 1 of FIG. 4, respectively. These values of $r_{min}$ can be substituted in Eq. (1) to calculate the absolute maximum intensity experienced by the particle.

Determination of particle size with laser light scattering instruments has always been complicated by the fact that peak signal levels $S_{max}$ ($S_1$ or $S_2$ in FIG. 5) from a scattered light transducer which are quite convenient to measure depend on both particle properties and incident intensity:

$$S_{max}(d,n) = C(d,n,g) I_{max} \tag{8}$$

Here C represents a partial light scattering cross-section which is a function of particle properties (diameter d and index of refraction n) through for example Lorenz-Mie light scattering theory, as well as instrument geometry (g) through detector fields of view in relation to the particle light scattering coordinate system. $I_{max}$ is the maximum incident intensity on the particle, e.g. $I_1$ 37 in FIG. 5. The resulting ambiguity between peak signals from small particles traversing the laser beam center and larger particles passing through the beam at off center positions of lower intensity has previously rendered absolute scattering signal amplitudes nearly useless for particle sizing.

This invention permits an entirely new approach. The peak incident intensity on a particle 37 is effectively measured through traverse properties $V_\perp$, $\theta$ and $y_c$ determined as discussed above. The measured peak scattering signals $S_{max}$ are then divided by this calculated $I_{max}$ such that C in Eq. (8) is measured. The choice of detector configuration determines which particle property most strongly influences C, and a measure of that particle property can be determined.

Figure 6:
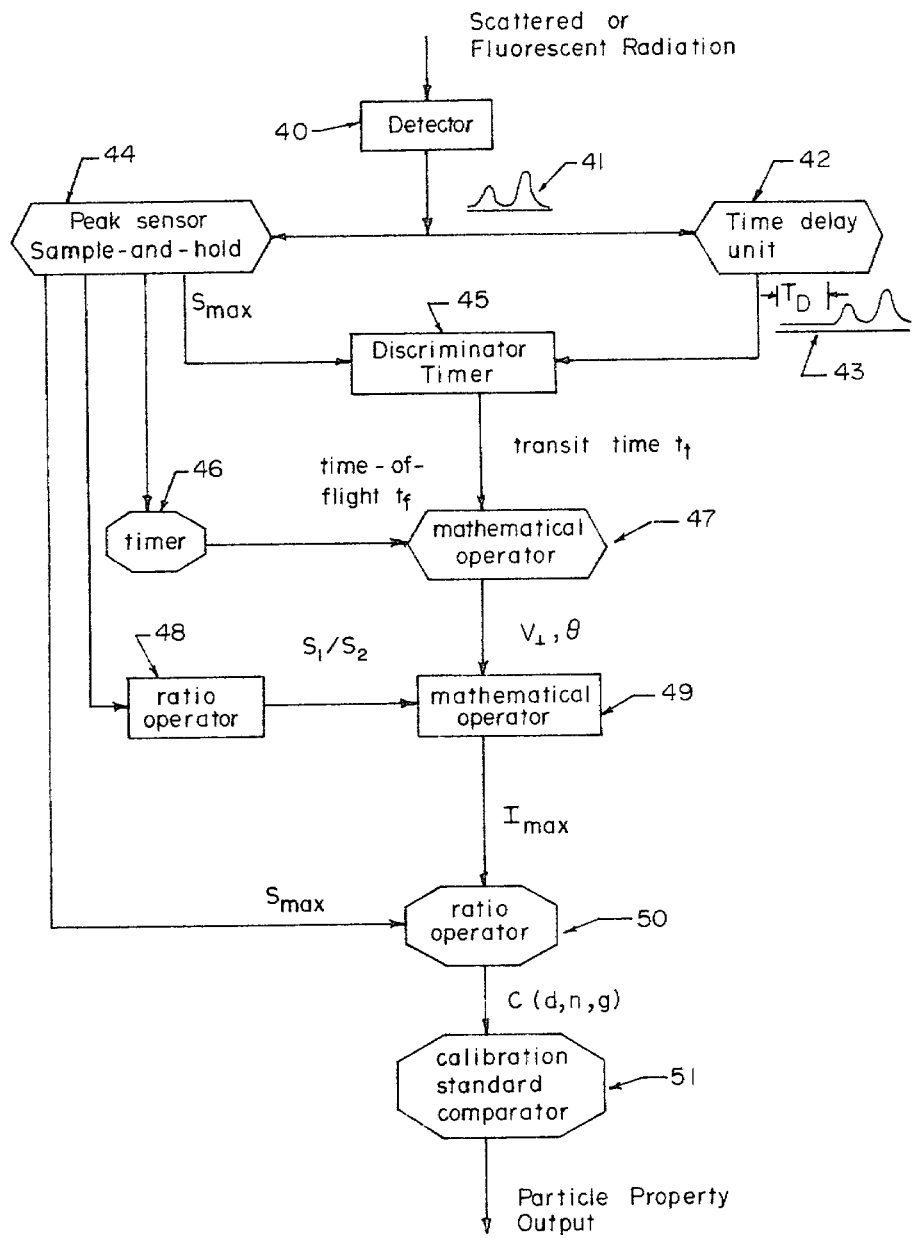
FIG. 6 is a block diagram of a possible data processing system for the present invention.

FIG. 6 is a schematic of data acquisition electronics for the present invention. Radiation from a particle incident on a detector 40 generates a signal 41 as in FIG. 5. The transit-time or width of the signal at a level corresponding to a constant fraction of the peak level must be measured. However on the leading edge of the signal the peak level is still unknown, so the signal is split and sent through a delay unit 42. The delay unit gives the original signal back but delayed in time $t_D$ 43. In the meantime the original signal is analyzed by a peak sensor 44 which sets a discriminator 45 to start and stop a timer at the constant fraction of peak signal level to measure $t_t$. A timer 46 also measures the time-of-flight between the peaks detected by the peak sensor. The measured $t_t$ and $t_f$ are then used to find $V_\perp$ and $\theta$ with a mathematical operator 47. The peak detector also provides the peak signal levels to a ratio circuit 48 to calculate $S_1/S_2$ which is used with $V_\perp$ and $\theta$ to electronically calculate $I_{max}$ 49. Then the peak signal level $S_{max}$ is divided by $I_{max}$ 50 which determines C, and the particle property of interest is found 51 from C and a calibration standard. The operations in units 47, 49 and 51 could also be performed by a minicomputer which was input $t_t$, $t_f$, $S_1$ and $S_2$.

The concept of this invention can be readily extended to other measurement systems. An additional parallel beam to make a triangular pattern in FIG. 4 could be added to provide two measures of particle velocity and size for comparison. The beams could also be rotated about a parallel line centered between them to vary $\theta$ for a given particle trajectory. An additional beam or pair of beams pointing in another direction could be added to provide further information on the third particle velocity component. All of these alterations would be obvious extensions of the present invention and therefore not unique inventions.

I claim:

1. In a system for determining two velocity components and at least one of the physical properties of a particle passing through a particle sampling zone and including: means for generating two beams of electromagnetic radiation with radially symmetric intensity distributions and for passing said beams of radiation through said zone whereby a portion of said radiation is incident on and is scattered by said particle; detective means responsive to said scattered radiation for developing a signal indicative of the temporal history of the magnitude or intensity of said radiation incident on said particle during the traverse through said sampling zone where said signal contains two signal pulses separated in time resulting from said particle passing through each of the two said beams in said sampling zone in succession; means responsive to said signal to determine the speed or velocity magnitude of said particle in the geometric plane normal to said beams from the shape of at least one of the two signal pulses; means responsive to the time between said two signal pulses in conjunction with said speed measurement to determine the two velocity components in said plane; means responsive to said two signal pulses in conjunction with said two velocity component measurement to determine an absolute measure of said radiation intensity incident on said particle during passage through said sampling zone; and means responsive to said signal pulses in conjunction with said measure of said incident radiation intensity to determine a measure of at least one of the physical properties of said particle.

2. The system set forth in claim 1 wherein said beams of radiation are generated by a laser operating in the $TEM_{oo}$ or fundamental mode whereby said radially symmetric intensity distributions will be gaussian and therefore said two signal pulses from said particle will also be of gaussian shape.

3. The system set forth in claim 2 wherein said means to determine said particle speed comprise measurement of the transit-time or width of said gaussian signal pulses at some constant fraction of the peak signal level and including means for measuring the actual spatial width of said gaussian laser beams at said constant fraction of the peak beam intensity and means for determining said particle speed from said spatial width traveled in said measured transit-time.

4. The system set forth in claim 2 including means for measuring the spacing between said beams and wherein the time-of-flight or time between the peaks of said signal pulses from said two beams in conjunction with said measured particle speed and spacing determines said angle of said particle traverse and thereby determines said two velocity components in said plane.

5. The system set forth in claim 2 wherein the ratio of said peaks of said signal pulses in conjunction with said measured particle speed and angle determines the position at which the particle traversed said sampling volume, and wherein said determined position and angle are used to calculate the maximum intensity of said incident laser radiation on said particle, and including means for determining a measure of the size of said particle from said peaks of said signal pulses normalized by said calculated maximum intensity incident on said particle.

6. The system set forth in claim 5 including means for determining a measure of the refractive index and therefore composition of said particle in conjunction with said measure of particle size and peaks of signal pulses normalized by said calculated maximum incident intensity from an additional detector sensitive to the refractive index of said particle.

7. The system set forth in claim 1 wherein said detective means are two detectors used with each of said detectors receiving said scattered radiation from said particle only when said particle is in one of said beams in the sampling zone and including means responsive to signals from both of said detectors for determining which of said beams said particle passed through first and thereby for determining the direction of the velocity of said particle.

8. The system set forth in claim 7 wherein said two beams are of different color and said detectors are selectively color sensitive for both velocity and particle property measurement.

9. The system set forth in claim 1 wherein said signal from a particle which passes through only one of said beams in said sampling volume can be identified as a partial or incomplete signal and said partial signal eliminated from further consideration by resetting said means responsive to the time between the two said signal pulses.

10. The system set forth in claim 1 wherein said means responsive to said shape of either of said signal pulses includes means for comparing said speeds calculated from the shape of both of said signal pulses and means for eliminating said particle signal from further consideration if said speeds do not agree to within some acceptable error band.

11. The system set forth in claim 1 wherein a portion of said radiation incident on said particle is partially absorbed and re-emitted as fluorescence by said particle and said signal is developed by detective means responsive to said fluorensence.

12. The system set forth in claim 11 wherein said detective means are two detectors used with each of said detectors receiving said fluorescent radiation only when said particle is in one of said beams in the sampling zone and including means responsive to signals from both of said detectors for determining which of said beams said particle passed through first and thereby for determining the direction of the velocity of said particle.

13. The system set forth in claim 11 wherein fluorescent radiation signal pulses determine said velocity components and said absolute measure of incident radiation intensity and said measure of particle size is indicative of the volume of the particle.

14. The system set forth in claim 1 wherein said measured physical particle property is particle size.

* * * * *